US012669322B2

(12) United States Patent
Lankenau

(10) Patent No.: US 12,669,322 B2
(45) Date of Patent: Jun. 30, 2026

(54) METHOD FOR TESTING AN OCT DEVICE AND TEST OBJECT

(71) Applicant: Eva Lankenau, Langstedt (DE)

(72) Inventor: Eva Lankenau, Langstedt (DE)

( * ) Notice: Subject to any disclaimer, the term of this patent is extended or adjusted under 35 U.S.C. 154(b) by 228 days.

(21) Appl. No.: 18/393,013

(22) Filed: Dec. 21, 2023

(65) Prior Publication Data

US 2024/0219168 A1      Jul. 4, 2024

(30) Foreign Application Priority Data

Dec. 22, 2022    (DE) .......................... 102022134628.5

(51) Int. Cl.
*G01B 9/02055* (2022.01)
*A61B 3/10* (2006.01)

(52) U.S. Cl.
CPC .......... *G01B 9/02067* (2013.01); *A61B 3/102* (2013.01)

(58) Field of Classification Search
CPC ............ G01B 9/02091; G01B 11/2441; G01B 9/02004; G01B 2290/70; G01B 9/0209; G01B 9/02044; G01B 9/02057; G01B 9/02; G01B 9/02083; G01B 9/02027; G01B 9/02087; G01B 11/0675; G01B 9/02007; G01B 9/0203; G01B 9/02084; G01B 2290/45; G01B 9/02072; G01B 11/14; G01B 9/02088; G01B 9/02069; G01B 9/02039; G01B 11/24; G01B 9/02063; G01B 9/0201; G01B 9/02028; G01B 2290/65; G01B 9/0207; G01B 11/06; G01B 9/021; G01B 9/0205; G01B 11/2513; G01B 9/02021; G01B 11/25; G01B 11/303; G01B 2290/60; G01B 9/02002; G01B 9/02077; G01B 11/22; G01B 2290/50; G01B 11/0625; G01B 2210/56; G01B 2290/35; G01B 11/005; G01B 9/02011; G01B 9/02064; G01B 9/02068; G01B 9/02078; G01B 9/02043; G01B 9/02058; G01B 11/02; G01B 21/042; G01B 11/026;
(Continued)

(56) References Cited

U.S. PATENT DOCUMENTS 7,924,435 B2 *    4/2011   Colonna De Lega ......................
G01B 9/02057
356/511
2004/0080759 A1 *    4/2004   Shaver ............... G02B 21/0028
356/609
(Continued)

FOREIGN PATENT DOCUMENTS

CN          108135466 A  *  6/2018  ......... G01B 9/02067
DE      102004013521 B4 *  4/2006  ......... G01B 11/2441
(Continued)

*Primary Examiner* — Michael P Stafira
(74) *Attorney, Agent, or Firm* — Alix, Yale & Ristas, LLP

(57) ABSTRACT

A method for testing an OCT device (14), in which a first test object (27) is arranged in an OCT beam path (16) of an OCT device (14). The first test object (27) comprises a layered structure (29) made up of a plurality of transparent layers and an entry body (30). OCT light emitted by the OCT device (14) enters the entry body (30) via an entry surface and propagates through the entry body (30) up to the layered structure (29). An entry surface of the entry body (30) is shaped as a lens surface (31). The invention also relates to a test object (27), which can be used in such a method.

12 Claims, 7 Drawing Sheets

(58) Field of Classification Search

CPC ............... G01B 9/02081; G01B 11/00; G01B 2210/50; G01B 5/008; G01B 9/02015; G01B 11/0608; G01B 11/161; G01B 11/255; G01B 21/045; G01B 9/02085; G01B 11/007; G01B 11/30; G01B 9/02048; G01B 9/02067; G01B 11/162; G01B 11/245; G01B 17/02; G01B 7/105; G01B 7/24; G01B 9/02012; G01B 9/02019; G01B 9/02089; G01B 9/04; G01B 11/002; G01B 11/2518; G01B 11/2545; G01B 11/26; G01B 9/02041; G01B 9/02054; G01B 9/02061; G01B 11/0633; G01B 11/306; G01B 21/04; G01B 5/28; G01B 9/02022; G01B 9/02032; G01B 9/02045; G01B 9/02075; G01B 11/024; G01B 11/164; G01B 15/045; G01B 21/20; G01B 9/02001; G01B 9/02074; G01B 11/08; G01B 11/2522; G01B 5/207; G01B 7/00; G01B 9/02005; G01B 9/02017; G01B 9/02049; G01B 9/02055; G01B 9/02059; G01B 11/0616; G01B 11/12; G01B 11/16; G01B 11/254; G01B 15/025; G01B 2290/15; G01B 2290/25; G01B 5/20; G01B 9/02035; G01B 11/0691; G01B 11/18; G01B 15/00; G01B 2290/30; G01B 7/003; G01B 7/06; G01B 7/16; G01B 7/34; G01B 9/02082; G01B 9/023; G01B 11/022; G01B 11/2504; G01B 11/2509; G01B 15/02; G01B 15/04; G01B 7/10; G01B 7/28; G01B 9/02024; G01B 9/02029; G01B 9/02034; G01B 9/02036; G01B 9/02037; G01B 9/02047; G01B 9/02051; G01B 9/02076; G01B 9/02097; G01B 1/00; G01B 11/0666; G01B 11/165; G01B 11/2527; G01B 17/025; G01B 21/085; G01B 21/16; G01B 2210/52; G01B 2210/58; G01B 2290/55; G01B 3/10; G01B 3/1061; G01B 7/281; G01B 9/02003; G01B 9/02018; G01B 9/02023; G01B 9/02025; G01B 9/02038; G01B 9/02042; G01B 9/02056; G01B 9/02071; G01B 9/02092; G01B 9/02095; G01B 9/02098; G01B 11/028; G01B 11/03; G01B 11/105; G01B 11/2408; G01B 11/272; G01B 13/10; G01B 15/06; G01B 17/08; G01B 21/047; G01B 21/22; G01B 21/30; G01B 3/008; G01B 3/1069; G01B 3/1084; G01B 3/11; G01B 3/22; G01B 3/36; G01B 3/40; G01B 5/0002; G01B 5/0014; G01B 5/004; G01B 5/06; G01B 5/201; G01B 5/252; G01B 5/30; G01B 7/02; G01B 7/023; G01B 7/285; G01B 9/02008; G01B 9/02009; G01B 9/02031; G01B 9/02052; G01B 9/02065; G01B 9/02079; G01B 9/02096

See application file for complete search history.

(56) References Cited

U.S. PATENT DOCUMENTS

| | | | | |
|---|---|---|---|---|
| 2009/0268161 A1 * | 10/2009 | Hart | ..................... | A61B 5/0066 |
| | | | | 351/208 |
| 2011/0181836 A1 * | 7/2011 | Rowe | ..................... | G09B 23/34 |
| | | | | 351/205 |
| 2012/0086948 A1 * | 4/2012 | Song | .................. | G01B 9/02091 |
| | | | | 356/479 |
| 2014/0072770 A1 * | 3/2014 | Hwang | ................ | A61B 5/0066 |
| | | | | 156/246 |
| 2019/0271533 A1 | 9/2019 | Robledo et al. | | |

FOREIGN PATENT DOCUMENTS

| | | | | | |
|---|---|---|---|---|---|
| DE | 102010046907 A1 * | 2/2012 | ......... | G01B 9/02056 |
| DE | 102011051146 B3 * | 10/2012 | ............... | G01B 9/02 |
| DE | 102015122842 A1 * | 6/2017 | ............ | G01C 25/00 |
| DE | 102018207827 B3 | 8/2019 | | |
| DE | 102018010287 A1 | 11/2019 | | |
| DE | 102021113074 B3 * | 8/2022 | ............ | G09B 23/30 |
| EP | 3182062 B1 | 9/2021 | | |
| JP | 2008304314 A * | 12/2008 | | |
| JP | 2013144047 A * | 7/2013 | ......... | G01B 9/02091 |
| KR | 20230099309 A * | 7/2023 | ............... | G02B 5/20 |
| WO | WO-2020198562 A1 * | 10/2020 | ............ | A61B 3/005 |

* cited by examiner

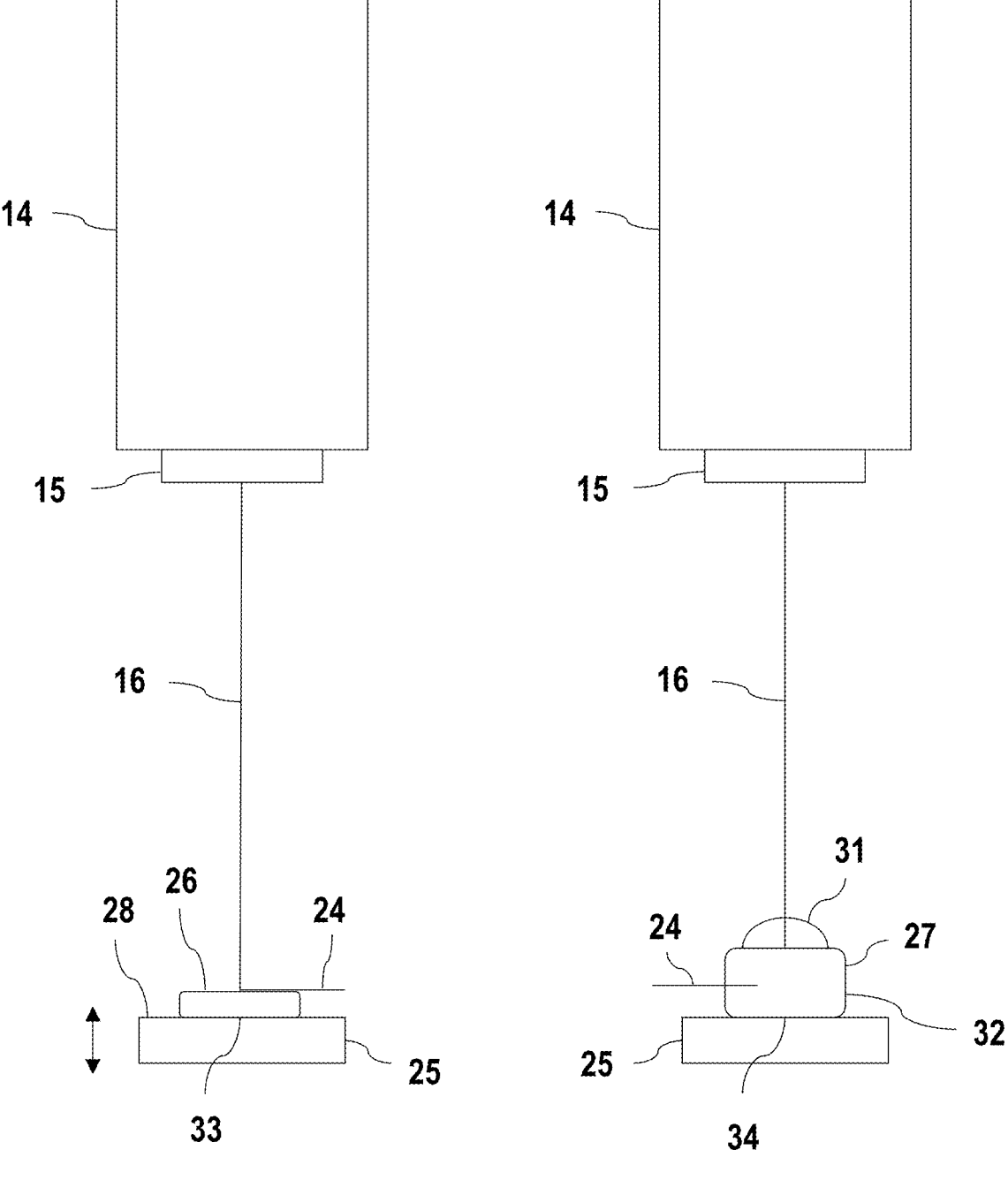
Fig. 4                Fig. 5 z z

METHOD FOR TESTING AN OCT DEVICE AND TEST OBJECT

BACKGROUND

The invention relates to a method for testing an OCT device and a test object.

Optical coherence tomography (OCT) is an imaging measurement method in which OCT light is guided onto an object, in particular human tissue. Scattering centers in the object are concluded from reflected components of the OCT light. For this purpose, components of the object beam path reflected from the object are superimposed with a reference beam path to generate an interference signal. OCT image information is obtained by evaluating the interference signal.

The axial measurement depth is limited in OCT measurements. For a high signal strength of the interference signal, it is necessary to set the reference plane and the focus of the OCT beam path correctly. The reference plane designates a plane in the OCT beam path in which the length of the object beam path and the length of the reference beam path correspond. This reference plane can have the depth position $z=0$ mm in the so-called OCT measurement window.

Testing OCT devices has been linked up to this point with a high level of effort. To determine how the signal strength changes with increasing distance from the reference plane, a test object can be introduced into the object beam path and the OCT device can be focused on the test object. If the optical path length in the reference beam path is changed in the measurement setup, which is otherwise unchanged, the signal strength of the interference signal obtained from the test object thus changes as a function of the axial distance between the reference plane and the planar surface. This change of the signal strength is referred to as the OCT roll-off.

In such a measurement, the signal strength of the interference signal is often greater than in the case of normal OCT measurements, which can result in oversaturation of the OCT signal. To avoid the oversaturation, the measurement can be carried out using reduced intensity of the OCT light in the object beam path, which has the disadvantage, however, that the conditions in the testing measurement are not identical to the conditions in a normal OCT measurement.

To determine the numerical aperture, the focus position, and the lateral resolution of the OCT device, a test object can also be introduced into the object beam path so that the OCT device is focused on the test object. If the test object is now moved in the axial direction with constant length of the reference arm, both the distance from the reference plane and the distance from the focal position of the object beam path change. The change in the signal strength of the interference signal resulting therefrom can be measured. The intensity of the object beam path also regularly has to be reduced here to avoid oversaturation of the interference signal.

SUMMARY

The invention is based on the object of presenting a method for testing an OCT device and a test object using which these disadvantages are avoided. The object is achieved by the features of the independent claims. Advantageous embodiments are specified in the dependent claims.

In the method according to the invention for testing an OCT device, a first test object is arranged in an OCT beam path of an OCT device. The first test object comprises a layered structure made of a plurality of transparent layers and an entry body. OCT light emitted by the OCT device enters the entry body via an entry surface and propagates through the entry body up to the layered structure. The entry surface of the entry body is shaped as a lens surface.

The invention proposes using interference signals obtained from the layered structure of the first test object for testing the OCT device. The layered structure is arranged inside the body of the first test object, due to which it is possible to keep the index of refraction jumps small at the interfaces, from which the interference signal is obtained. Between the entry surface and the layered structure, the OCT light propagates within the entry body so that the index of refraction jump can also be kept small at the first layer of the layered structure and an oversaturated interference signal can be avoided. The focus of the object beam path can be positioned in a suitable manner by the entry surface of the entry body shaped as a lens surface.

The layered structure can be adapted to the axial resolution of the OCT device, which is often in the order of magnitude between 1 µm and 50 µm. For example, the layered structure can comprise layers, the thickness of which is between 20 µm and 500 µm, preferably between 50 µm and 200 µm. It is advantageous if the layered structure comprises multiple layers which are of equal thickness, the thickness of which thus corresponds insofar as it may be implemented in the manufacturing. The number of the layers in the layered structure can be, for example, between 5 and 50, preferably between 10 and 30. Each of the layers can have the mentioned features.

Adjoining layers of the layered structure can consist of different materials. Layers which do not adjoin one another can consist of the same material. In one embodiment, the layered structure is constructed from two different materials, wherein the layers alternately consist of the first material and the second material.

To avoid oversaturation of the OCT signal, it is advantageous if the index of refraction difference between adjoining layers of the layered structure is not excessively large. For example, the index of refraction difference between the materials of two adjoining layers can be less than 0.1, preferably less than 0.075, more preferably less than 0.05. The index of refraction difference should not be below 0.001, because the signal obtained is otherwise no longer sufficiently strong. This preferably applies for each layer transition of the layered structure. All specifications on index of refraction differences relate to the central wavelength of the OCT light.

For example, glass materials, epoxy resins, optical adhesives and silicones come into consideration as transparent materials for the layered structure. One or more layers of the layered structure can consist of an optical adhesive with a group index of refraction $n_g$ between 1.45 and 1.55. Optical adhesives are transparent and are characterized by the fact that the refractive index is well defined and lies within a specified range. It is also possible that one or more layers of the layered structure consist of a silicone material having a group index of refraction of $n_g(840 \text{ nm})$ between 1.41 and 1.49. One or more layers of the layered structure can consist of a glass material having a group index of refraction of $n(840 \text{ nm})$ between 1.45 and 1.55, preferably between 1.46 and 1.55. One or more layers of the layered structure can consist of an epoxy resin having a group index of refraction $n(840 \text{ nm})$ between 1.47 and 1.56. In one embodiment, one or more layers of the layered structure consist of borosilicate glass D263 M with $n_g(840 \text{ nm})=1.516$. A material is designated as transparent if an OCT beam path can continue within the material. It is advantageous if the materials of the first test object are essentially glass clear.

In one possible layered structure, layers made of borosilicate glass alternate with layers made of an optical adhesive. It is also possible that layers made of borosilicate alternate with layers made of a silicone material. In an alternative embodiment, layers made of borosilicate glass alternate with layers made of epoxy resin in the layered structure. The layered structure can be created in that the layers made of glass are provided as prefinished parts. The prefinished parts can be laid in the other material, which is still in a liquid state, so that after the hardening of the other material, a layered structure made of glass and the other material results. If the prefinished parts are held at a suitable distance from one another even without hardening of the other material, a layered structure is also possible in which layers consist of a permanently liquid material, for example, of silicone oil. Intermediate layers between glass and the other material should be avoided. This applies in particular to air inclusions between glass and the other material.

The entry body arranged between the entry surface of the first test object and the first layer of the layered structure can consist of a uniform material, so that the entry body is free of index of refraction jumps. The surface via which the OCT beam path enters the material of the first test object is designated as the entry surface of the first test object. The index of refraction difference between the material of the entry body and a layer of the layered structure adjoining the entry body can be less than 0.1, preferably less than 0.075, more preferably less than 0.05. The index of refraction difference should also not be less than 0.001 here. The material of the entry body can be a material which is mentioned above as a suitable material for layers of the layered structure. In one embodiment, the material of the entry body is an optical adhesive, a silicone material or an epoxy resin and the material of the first layer of the layered structure is a glass material. During the production of the first test object, the first layer of the layered structure can be laid in the material of the entry body as long as the material of the entry body is still liquid. The first test object is preferably designed so that there are no inclusions of further materials, in particular no inclusions of air, between the entry surface and the layered structure.

An index of refraction jump is connected to the entry into the body of the test object, which corresponds to the difference between the index of refraction of air (approximately n=1) and the index of refraction of the material of the entry body. If the entry body consists of one of the above-mentioned materials, an index of refraction difference between 0.4 and 0.6 thus results. At such a high index of refraction difference, the proportion of the reflected OCT light is sufficiently high that the signal of a typical OCT device calibrated for smaller index of refraction differences will be oversaturated. The method is therefore preferably carried out so that the entry surface of the first test object lies outside the measuring window of the OCT device. The measuring window designates that axial range of the OCT beam path from which items of image information are obtained using the OCT measurement. The measuring window can extend, for example, over several millimeters in front of and/or behind the reference plane.

The distance between the layered structure and the lens surface is preferably greater than 30%, more preferably greater than 50%, more preferably greater than 80% of the axial length of the measuring window. In absolute numbers, the distance between the layered structure is preferably greater than 3 mm, preferably greater than 5 mm, more preferably greater than 8 mm. All specifications with respect to a distance to the lens surface relate to the apex of the lens surface. If the layered structure has a thickness of 10 mm, this corresponds to an optical path length of approximately 15 mm. This is more than the depth of typical OCT measuring windows, which is usually between 2 mm and 14 mm.

The propagation speed of the OCT light in the body of the test object is reduced accordingly with the ratio of the indices of refraction. Due to the reduced propagation speed, the reference plane of the OCT measurement within the test object is at a smaller distance to the entry surface than in an air path measurement. In an air path measurement, the OCT light propagates between the OCT device and the OCT measuring window within air. Formulated inversely, a structure detected within the test object appears to be at a greater distance than it actually is with an OCT device calibrated on an air path. If a structure has a distance of 10 mm to the entry surface of the test object and the material of the test object has an group index of refraction $n_g(840 \text{ nm})=1.5$, for example, the structure appears to have a distance of 15 mm to the entry surface in the OCT measurement.

If the test object had a planar entry surface, the focal position of the OCT beam path would thus shift accordingly. In the above example, if an air path measurement had a focal position 10 mm behind the position of the entry surface, the geometric focal position in the case of a test object having planar entry surface would thus be 15 mm behind the entry surface. The introduction of a test object into the beam path of an OCT device calibrated on an air path generally results for this reason in a shift between the reference plane of the OCT measurement and the focal position of the OCT beam path. The invention proposes designing the entry surface of the test object as a lens surface to counteract this shift of the focal position.

The lens surface can be shaped so that the distance between the focal position of the OCT beam path and the reference plane of the OCT measurement is reduced, preferably is reduced by at least 30%, more preferably is reduced by at least 50%, more preferably is reduced by at least 70% in comparison to a test object which has a planar entry surface instead of the lens surface. The lens surface can additionally or alternatively thereto be shaped so that the difference between the geometric focal position in the first test object and the geometric focal position in the air path is reduced, preferably is reduced by at least 30%, more preferably is reduced by at least 50%, more preferably is reduced by at least 70% in comparison to the case that instead of the first test object, a test object having a planar entry surface is introduced into the beam path. In particular, the lens surface can be shaped so that the geometric focal position within the test object is the same as the focal position in the air path, thus when no test object is arranged in the OCT beam path. For these comparisons, it is presumed that the planar entry surface is arranged in a position which corresponds to the point of the lens surface which has the least distance to the OCT device. In general, this is the apex of the lens surface.

If an OCT device is not used to examine the front section of the eye, but rather to examine the retina, the OCT beam path is thus incident in the collimated state on the cornea. The focusing of the OCT beam path on the retina first results due to the optical elements in the front section of the eye, thus in particular the cornea and the eye lens of the patient eye. The first test object can also be used to test such an OCT device by positioning a lens in front of the lens surface of the first test object which shapes the incident collimated OCT beam path so that the focus of the OCT beam path is within the layered structure. The refractive power of such a lens essentially corresponds to the cornea and the eye lens of a patient eye.

In one embodiment, in the method according to the invention, a set of test objects is used, wherein the set comprises a first test object which is designed according to the invention and wherein the set comprises an alternatively designed second test object. It can be determined using the second test object where the OCT measuring window lies by moving the second test object in the z direction until the OCT device supplies an image of a test surface of the second test object. The axial distance between the second test object and the OCT device is changed by a movement in the z direction.

The second test object can have a nonreflective test surface, on which incident OCT light is scattered. The test surface can be provided with a test structure, which has a known spatial distribution. The test structure can be designed as a three-dimensional structure of the test surface. In one embodiment, the test structure comprises a plurality of concentric circles.

The size of the image field of an OCT measurement can be determined by a second test object having such a test structure. For this purpose, the second test object can be positioned in the z direction so that the OCT device generates an image of the test surface. With a circular test structure, the OCT beam path can be aligned perpendicular to the z direction on the center point of the circular structure. If an image of the test surface is generated using the OCT device, the size of the image field of the OCT measurement can thus be read by a comparison of the image to the actual test surface.

The method can be carried out so that the second test object rests on a positioning surface and the positioning surface and the OCT device are moved relative to one another in order to focus the OCT device on the test surface. Following an OCT measurement, the second test object can be removed from the positioning surface to enable a subsequent measurement using the first test object according to the invention.

If the distance between the OCT device and the positioning surface is maintained unchanged, it can thus be determined on the basis of the known parameters of the first test object which distance the lens surface has to have from the positioning surface so that the focus of the OCT beam path falls in the layered structure of the first test object. The first test object can have a contact surface opposite to the lens surface, wherein the distance between the contact surface and the lens surface is dimensioned so that the layered structure lies in a z position which is visible in the OCT measurement, which thus lies within the OCT measuring window. The OCT device is preferably positioned relative to the first test object so that the layered structure overlaps the OCT measuring window, that the layered structure thus covers the entire depth of the recorded OCT image. With a correctly adjusted OCT device, the focus of the OCT beam path then also lies within the layered structure. The OCT device can be set so that the reference plane of the OCT measurement coincides with the near end of the OCT measuring window.

The first test object and the second test object can be matched to one another so that the OCT beam path is focused on a test surface of the second test object when a contact surface of the second test object is arranged at a predetermined axial distance to the OCT device and the OCT beam path is focused within the layered structure of the first test object if the first test object is arranged in the OCT beam path instead of the second test object and a contact surface of the first test object has the same axial distance to the OCT device.

If an OCT measurement is carried out on the first test object using such a measurement setup, the obtained measurement signal thus has a peak at each of the interfaces of the layered structure. The depth of the OCT measuring window can be calculated directly from the number of the peaks visible in the measurement and on the basis of the known dimensions of the layered structure.

In a diagram in which the amplitude of the measurement signal is plotted over the z position, a curve may be generated which connects the maxima of the peaks to one another. In OCT, the measured amplitude values are typically logarithmized. If the signal S is measured by the detector, for example, the amplitude $A=20*\log(S)$ is stored. The invention proposes fitting the curve using the following equation.

$$A_{max}(z) = 10 \cdot \log\left(\frac{I_0}{1 + \left(\frac{z - z_0}{\Delta z}\right)^2}\right) + A_{roll-off}$$

In this equation, z is the variable which corresponds to the position of the peak maximum $A_{max}$ in the diagram. In this equation, the component $A_{roll-off}$ corresponds to the OCT roll-off. The other component of the equation stands for the expansion of the OCT beam with increasing distance from the OCT focus position $z_0$.

The roll-off can be approximated by the following formula, which decreases towards the end of the OCT measurement window:

$$A_{roll-off} = \frac{\sin((z - z_{roll}) \cdot a)}{(z - z_{roll}) \cdot a} \cdot b$$

Alternatively, a simplifying assumption can also be made that the roll-off has a linear progression that can be fitted with a*z+b.

$\Delta z$ is the Rayleigh length of the OCT beam. The Rayleigh length $\Delta z$ corresponds to the distance in the z direction over which the OCT beam doubles its cross-sectional area starting from the focus position $z_0$. The focus position $z_0$ corresponds here to the z position in which the OCT beam path has the smallest cross section, thus the z position of the smallest constriction of the OCT beam. The constants $I_0$ and b are required to be able to fit the course of the peak maxima $A_{max}(z)$ with the equation. The relevant variables in the equation which have a relationship to properties of the OCT device are the OCT focus position $z_0$, the Rayleigh length $\Delta z$, and the OCT roll-off constants $z_{roll}$ and a.

The OCT roll-off constants $z_{roll}$ and a are independent of the optics of the first test object and can therefore be transferred directly to air path measurements. In contrast, the determined values for the OCT focus position $z_0$ and the Rayleigh length $\Delta z$ relate to the conditions within the first test object. A transfer to air path measurements requires a conversion on the basis of the known optical parameters of the first test object.

The method according to the invention has the advantage of improved resolution over alternative methods in which the relevant parameters of the OCT device are determined directly on the basis of an air path measurement. This results because a smaller Rayleigh length $\Delta z$ and thus a higher numeric aperture of the OCT beam path result due to the refraction properties of the first test object. A further advantage lies in the insensitivity to adjustment of the method according to the invention. This means that it has no detrimental effect on the measurement if the test object is not exactly aligned with the optical axis but is tilted by a few degrees, for example. This differs from alternative methods in which the OCT beam path is reflected at a mirror to test the OCT device.

An interface between two layers of the layered structure has no extension in the axial direction, because of which the axial resolution of the OCT device can be concluded from the width of a peak generated at such an interface. It is to be taken into consideration here that the peaks are wider due to the group-velocity dispersion GVD in the material of the first test object than in the case of an air path measurement. The conversion to the full width at half maximum for a peak of the air path measurement is carried out using the following formula $$\delta z_{ph} = \sqrt{\delta z_{air}^2 + (c \cdot GVD(\lambda_c) \cdot d \cdot \Delta\lambda)^2}$$

In this formula, $\delta z_{air}$ is the axial resolution of the OCT device in air, which ideally corresponds to the coherence length $I_C$ of the OCT light source, which at the same time corresponds to the best possible axial resolution achievable using the OCT device. The parameter d stands for the distance over which the beam path propagates within the material of the first test object. Ac is the central wavelength of the OCT light and AA is the spectral width of the OCT light source. The wavelength-dependent group-velocity dispersion $GVD(\lambda)$ of the material within which the OCT light propagates is known. The width $\delta z_{ph}$ of the peak, which corresponds to the axial resolution within the test object, is read from the measured data. Solved for $\delta z_{air}$ (resolution in air) the coherence length $I_C$, the relationship is as follows.

$$\delta z_{air} = \sqrt{\delta z_{ph}^2 - (c \cdot GVD(\lambda_c) \cdot d \cdot \Delta\lambda)^2}$$

The relevant parameters for an air path measurement can thus be derived from the measurement according to the invention.

In addition, it is also possible to derive an estimate about the image field curvature from a measurement performed using the first test object. For this purpose, it is necessary to know the image field size. Furthermore, it has to be taken into consideration that in the measurement according to the invention, an image field curvature is also caused by the material of the first test object. The component of the image field curvature caused by the first test object has to be calculated out in order to be able to conclude the image field curvature with an air path measurement.

It is also possible to derive information about the numerical aperture of the OCT device from a measurement taken with the first test object. The scan width of the device can be determined for this purpose. The scan width is the range around the optical axis within which a signal can still be obtained with the OCT device. For a scan in a lateral direction, i.e. displacement of the OCT beam path transverse to the optical axis, the signal strength decreases with increasing distance from the optical axis. When the end of the scan width is reached, the signal disappears. The distance between the optical axis and this end of the scan range accessible with the measurement corresponds to half the scan width. It has been found that there is a linear relationship between the scan width and the numerical aperture. The scan width can easily be determined. Based on the known scan width, the numerical aperture of the OCT device can therefore be determined using a functional relationship between the scan width of the OCT measurement and the numerical aperture of the OCT device. The method according to the invention thus offers a simple way of determining a parameter of the OCT device that is otherwise only possible to determine with some effort.

It is also possible to derive information about the OCT sensitivity from a measurement taken with the first test object. The OCT sensitivity describes the smallest possible OCT signal to be detected and is therefore an important parameter for describing the quality of an OCT device. The amplitude in the OCT image behaves like the following formula:

$$A(z) \approx 20 \cdot \log\left(\sqrt{I_{ref} \cdot I(z)_{Probe}}\right)$$

$I_{ref}$ is the intensity of the OCT reference light and $I(z)_{Probe}$ is the light intensity that comes back into the device from the respective depth of the test specimen.

The depth-dependent noise signal $A_{noise}$ can be determined from an OCT measurement without a test specimen. The maximum amplitude $A_{max,fokes}$ in the focal plane can be determined from the OCT measurement of the test specimen. This gives the signal-to-noise ratio of the OCT measurement of the test specimen with:

$$SNR = (A_{max,focus} - A_{noise}) \cdot F$$

The amplitude $A_{max,focus}$ in the test specimen is reduced by a factor F compared to the amplitude without group dispersion velocity (i.e. a measurement in air). This factor can be determined. For example, SNR=53.2 dB. The reflectivity of a layer transition in the test specimen is also known and is calculated using the following formula:

$$R(z_{focus}) = \left(\frac{n_1 - n_2}{n_1 + n_2}\right)^2 = \frac{I(z_{focus})_{Probe}}{I_{0,Probe}}$$

Where $n_1$ is the refractive index of the first layer material and $n_2$ is the refractive index of the second layer material. $I_{0,Probe}$ is the light intensity irradiated onto the test specimen and $I(z_{focus})_{Probe}$ is the light intensity that comes back into the OCT device from the focal plane of the test specimen. For the test specimen described here, for example, the reflectivity of a layer transition is R=0.00002. This corresponds to an OCT specimen light intensity of 10*log(R)=−47 dB. The maximum amplitude measured in the specimen in the focal plane is reduced by 10*log(R) to obtain the sensitivity of the OCT device.

$$Sensitivität = SNR - 10 \cdot \log(R(z_{focus}))$$

In our example, 53.2 dB−(−47 dB)=100.2 dB.

The invention also relates to a test object which is intended for use in testing an OCT device. The first test object comprises a layered structure made of a plurality of layers and an entry body. The layered structure and the entry body consist of materials transparent to OCT light. An entry surface of the entry body is shaped as a lens surface. Such a test object can be used as the first test object in the meaning of the method according to the invention.

The disclosure comprises refinements of the test object having features which are described in the context of the method according to the invention. The disclosure comprises refinements of the method having features which are described in the context of the test object according to the invention.

BRIEF DESCRIPTION OF THE DRAWINGS

The invention is described hereinafter by way of example with reference to the appended drawings on the basis of advantageous embodiments. In the figures:

FIG. 4: shows the OCT device from FIG. 1 during a measurement on a second test object;

FIG. 5: shows the OCT device from FIG. 1 during a measurement on a first test object;

DETAILED DESCRIPTION

Figure 1:
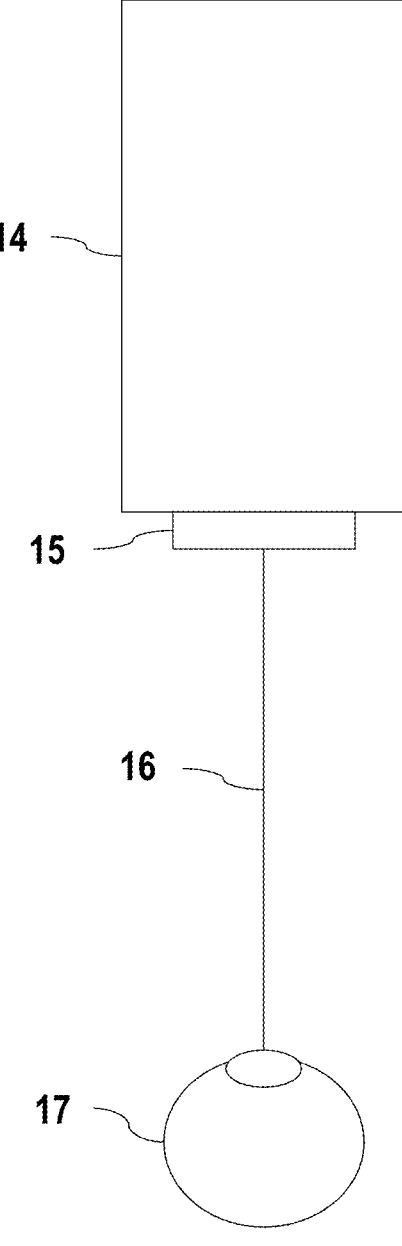
FIG. 1: shows a schematic representation of an OCT device during use on a human eye.

An OCT device 14 shown in FIG. 1 has an exit opening 15, through which an OCT beam path 16 generated in the OCT device is directed as the object beam path on a human eye 17. Components of the OCT light scattered on the transparent structures in the front section of the eye 17 are reflected back into the OCT device 14 and brought to interference there with a reference beam path. The position of scattering centers in the eye 17 can be concluded from the interference signal. A scanning device (not shown) is formed in the housing of the OCT device 14, using which the OCT beam path 16 is deflected in the lateral direction so that the OCT beam path 16 scans the eye 17. The measurement data obtained using a single position of the OCT beam path 16 are designated as an A scan. A sectional image of the eye 17 (B scan) or a three-dimensional image of the eye 17 can be generated from a plurality of A scans.

Figure 2:
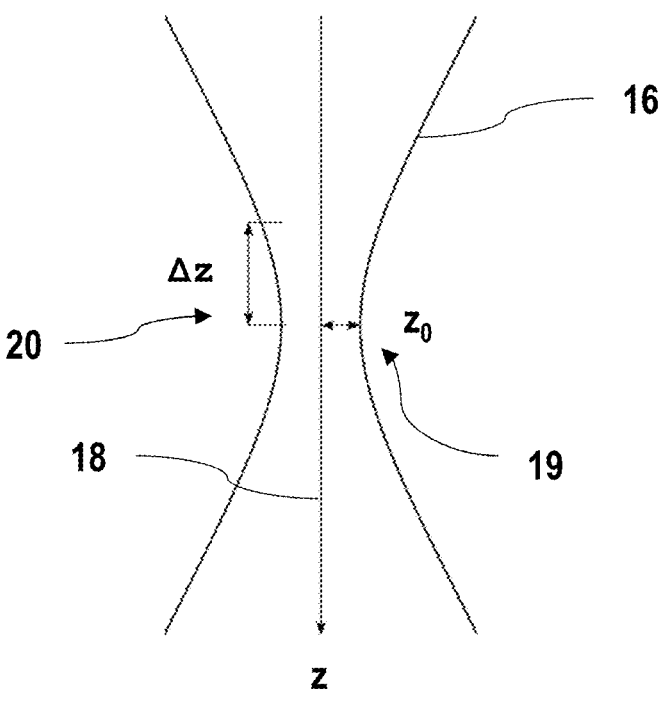
FIGS. 2, 3: show details of the beam path of the OCT device from FIG. 1.

According to FIG. 2, the OCT beam path 16 has a central beam 18 which extends in the z direction. With respect to the central beam 18, the OCT beam path 16 has a radial extension which has a smallest constriction 19 in a position $z_0$. The position $z_0$ corresponds to the focus of the OCT beam path 16. The cross-section of the OCT beam path 16 expands with increasing distance in the z direction from the smallest constriction 19. The distance $\Delta z$ within which the

10 cross-sectional area doubles starting from the smallest constriction 19 is designated as the Rayleigh length 20. Since the resolution of an OCT measurement becomes worse with increasing distance from the smallest constriction 19, the Rayleigh length 20 is a relevant parameter for the operation of an OCT device 14.

Figure 3:
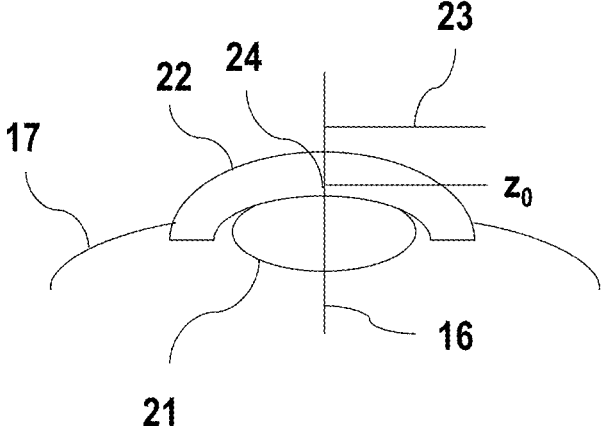

The OCT beam path 16 enters the transparent structures of the eye 17, which comprise a cornea 22 and an eye lens 21 according to FIG. 3. The focal position 24 in the position $z_0$ of the OCT beam path 16 lies within the transparent structures 21, 22. The reference plane 23 of the OCT measurement, in which the OCT beam path 16 (=object beam path) and the reference beam path have the same length is arranged in front of the cornea 22. The axial section, thus the section in the z direction, from which measurement data are obtained using the OCT measurement, is designated as the measuring window of an OCT measurement. The measuring window can comprise, for example, a range which extends from the front side of the cornea 22 to behind the eye lens 21.

After a period of time in which the OCT device 14 was used in examinations on patient eyes, a test of the OCT device is to be carried out. The test is to establish, inter alia, whether the OCT device 14 is correctly focused and whether the desired axial resolution is achieved over the measuring window.

In a first step of the test, the OCT beam path 16 is directed onto a second test object 26, see FIG. 4. The second test object 26 rests with a contact surface 33 on a measuring table 25, the surface of which forms a positioning surface 28. For the OCT recording, the OCT device 14 is set so that the focal position 24 of the OCT beam path 16 coincides with the upper side of the second test object 26.

A three-dimensional test structure in the form of concentric circles is formed on the upper side of the second test object 26. The second test object 26 consists of a nontransparent material, on the surface of which the OCT light is scattered. For a measurement, the second test object 26 is positioned in the lateral direction, thus perpendicular to the z direction, on the measuring table 25 so that the OCT beam path 16 strikes the center point of the test structure. During the measurement, the OCT beam is laterally deflected using a scanning device arranged in the housing of the OCT device 14, so that the OCT beam scans the surface of the second test object 26 in a scanning process.

Figure 6:
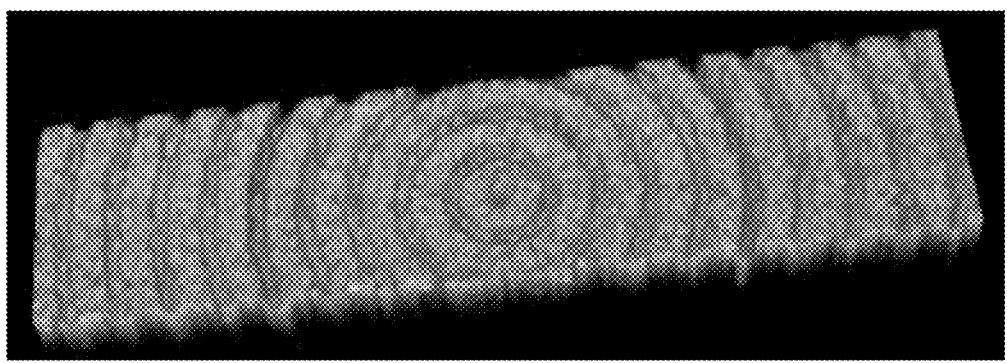
FIG. 6: shows an OCT image recorded on the second test object.

An OCT recording of the second test object 26 generated in this way is shown in FIG. 6. A rectangular detail of the surface is shown, in the center of which the center point of the test structure is arranged. The rings on the surface of the second test object 26 have a spacing of 200 μm. It can be derived from the number of the rings visible in FIG. 6 that the OCT device 14 is set to a lateral scanning width of 4 mm×1 mm.

In a second step of the test, the second test object 26 is removed from the measuring table 25 and a first test object 27 is positioned with its contact surface 34 on the measuring table 25. The distance between the OCT device 14 and the measuring table 25 remains unchanged.

The first test object 27 comprises a layered structure 29 and an entry body 30. The layered structure 29 comprises a total of twenty layers, which alternately consist of borosilicate glass D263M with n(840 nm)=1.516 and an optical adhesive NOA76 with n(840 nm)=1.504. The entry body 30, which directly adjoins the frontmost layer of the layered structure 29 consisting of borosilicate glass, also consists of the optical adhesive NOA76 with n(840 nm)=1.504. After the OCT beam path 16 has entered the body of the first test object 27, there are accordingly no more index of refraction jumps which are greater than 0.02. With such small index of refraction jumps, only a small part of the OCT light is reflected back in the direction of the OCT device 14, so that the intensity of the reflected OCT light is not greater than in the transparent structures in the front section of a patient eye 17. Oversaturation of the OCT signal is avoided.

The entry surface of the entry body 30, via which the OCT beam path 16 enters the body of the first test object 27, is shaped as a lens surface 31, due to which the focal position 24 of the OCT beam path 16 moves closer to the OCT device 14. The first test object 27 is designed so that the layered structure 29 has a distance in the z direction from the positioning surface 28 of the measuring table 25. The distance is dimensioned so that the layered structure 29 lies within the OCT measuring window of the OCT device. With a correctly configured OCT device 14, the focal position 24 of the OCT beam path 16 is then automatically within the layered structure 29. The measurement on the first test object 27 is preferably carried out so that the focal position 24 lies approximately in the middle within the layered structure 29. The reference plane of the OCT measurement can correspond to the near end of the OCT measuring window. If the first test object 27 were made of air, its surface would have to be shifted to plane 23 so that the layered structure 29 is visible in the OCT measuring window. The plane 23 of the OCT measurement is approximately at half the distance between the layered structure 29 and the apex of the lens surface 31. According to FIG. 5, the layered structure 29 and the entry body 30 are arranged in the test object 27 within a housing 32, the lower side of which forms the contact surface 34 of the first test object 27.

Figure 7:
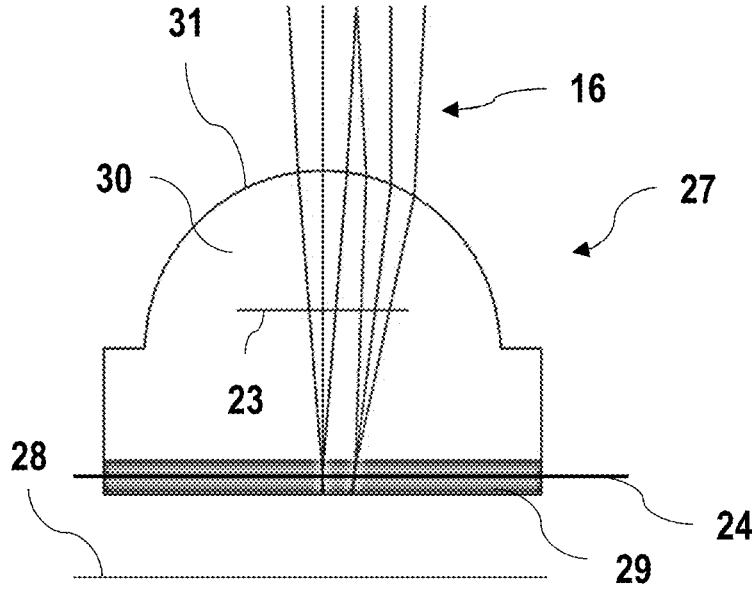
FIG. 7: shows a sectional view of a first test object.
Figure 8:
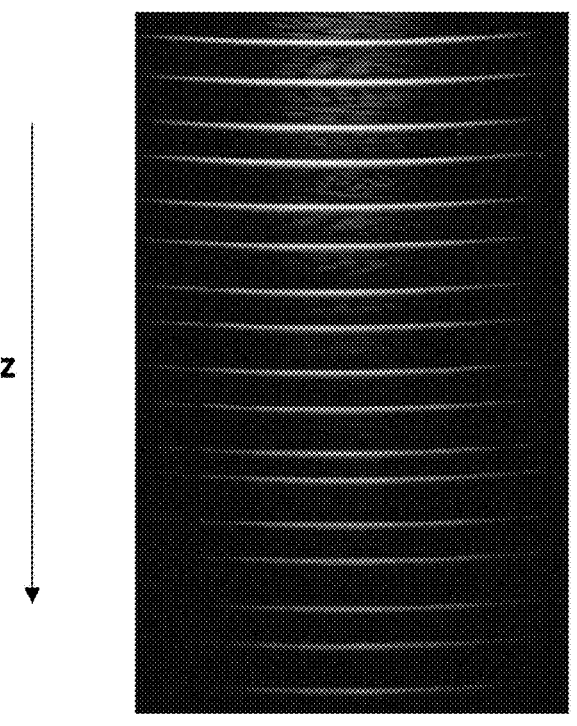
FIG. 8: shows an OCT image recorded on the first test object.

FIG. 8 shows an OCT recording in the form of a B scan recorded on the first test object 27. The B scan is obtained by scanning the first test object 27 using the OCT beam once in the transverse direction, for example, within the plane of the figure in FIG. 7. For each position of the OCT beam, an A scan is recorded, which results in image information pointing in the z direction into the depth of the first test object 27. The B scan is composed of a plurality of A scans.

Each interface between two layers of the layered structure 29 generates a peak of the interference signal, see the areas shown light in FIG. 8. The depth of the OCT measuring window can be read by counting the number of interfaces visible in the B scan.

The actually planar interfaces of the first test object 27 appear to have a slight curvature in FIG. 8. The image field curvature results because the OCT light propagates over a longer distance within the optical adhesive material of the entry body 30 before the layered structure 29. In a corresponding air path measurement, in which the OCT light propagates in air up to the beginning of the measuring window, the OCT device 14, using which the OCT recording in FIG. 8 was generated, would not display image field curvature. If an OCT recording obtained on the first test object 27 has a different image field curvature than in FIG. 8, the presence of an image field curvature can thus be concluded in air path measurements.

The interference signal shows a peak at each of the interfaces of the layered structure 29. The peaks of a single A scan are plotted in FIG. 9, wherein the horizontal axis corresponds to the z direction. The amplitude of the peaks decreases in two directions starting from a maximum. Two effects are superimposed in the decrease, namely once the increasing distance from the focal position 24 of the OCT beam path 16 and once the increasing distance from the reference plane 23 of the OCT measurement. The amplitude decreasing with increasing distance from the OCT reference plane 23 is designated as OCT roll-off.

Against this background, the amplitude course can be approximated by the following equation, in which both the distance from the focal position and the OCT roll-off are taken into consideration.

$$A_{max}(z) = 10 \cdot \log\left(\frac{I_0}{1+\left(\frac{z-z_0}{\Delta z}\right)^2}\right) + \frac{\sin((z-z_{roll}) \cdot a)}{(z-z_{roll}) \cdot a} \cdot b$$

Figure 9:
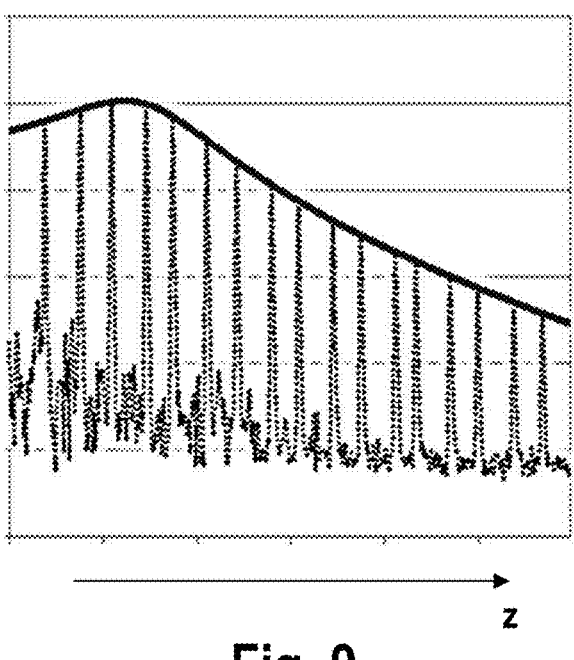
FIG. 9: shows an aspect of the OCT image from FIG. 8 in a different representation.

In this case, z is the variable which corresponds to the position of the peak maximum $A_{max}$ in FIG. 9. The sinc function corresponds to the OCT roll-off. The other component of the equation stands for the expansion of the OCT beam with increasing distance from the focal position 24. $\Delta z$ is the Rayleigh length 20 of the OCT beam. The constants $I_0$ and b are required to be able to fit the course of the peak maxima $A_{max}(z)$ using the equation. The variables relevant for testing the OCT device are the OCT focus position $z_0$, the Rayleigh length $\Delta z$, and the OCT roll-off constants $z_{roll}$ and a.

An OCT roll-off function results from the measurement in FIG. 9:

$$A_{roll-off} = \frac{\sin((z-z_{roll}) \cdot a)}{(z-z_{roll}) \cdot a} \cdot b$$

It is advantageous here to determine the value at 10% of the OCT measurement window depth minus the value at 90% of the OCT measurement window depth $A_{roll-off}$ (10% $z_{max}$)−$A_{roll-off}$(90% $z_{max}$). This value illustrates how much the OCT signal decreases with the measurement depth.

The focal position 24 can in an exemplary embodiment be in a position $z_0$, which lies 0.7 mm below the upper end of the measuring window. A value of $\Delta z$=0.58 mm is determined in this example for the Rayleigh length 20. A numeric aperture of 0.81 and a lateral resolution of 6.34 µm in the first test object result therefrom.

The OCT roll-off is independent of the optics of the first test object 27 and therefore also applies for an air path measurement on the patient eye, in which the OCT light propagates between the OCT device and the measuring window along an air path. In contrast, the determined values for the OCT focus position $z_0$ and the Rayleigh length $\Delta z$ relate to the conditions within the first test object. A transfer to the air path requires a conversion on the basis of the known optical parameters of the first test object.

OCT light having a central wavelength of A=840 nm was used for the measurement shown in FIG. 9. The material of the entry body 30 has a phase index of refraction n(840 nm)=1.50 and a group index of refraction $n_g$(840 nm)=1.51. The focal position and the Rayleigh length 20 for an air path measurement can be calculated on the basis of the information obtained using the measurement and the known geometric parameters of the first test object 27 and with application of Snell's law of refraction.

For the air path measurement, a numeric aperture of 0.036, a focal position $z_{0,air}$ of 1.26 mm below the upper end of the measuring window, and a lateral resolution of 14.36 µm result.

Figure 10:
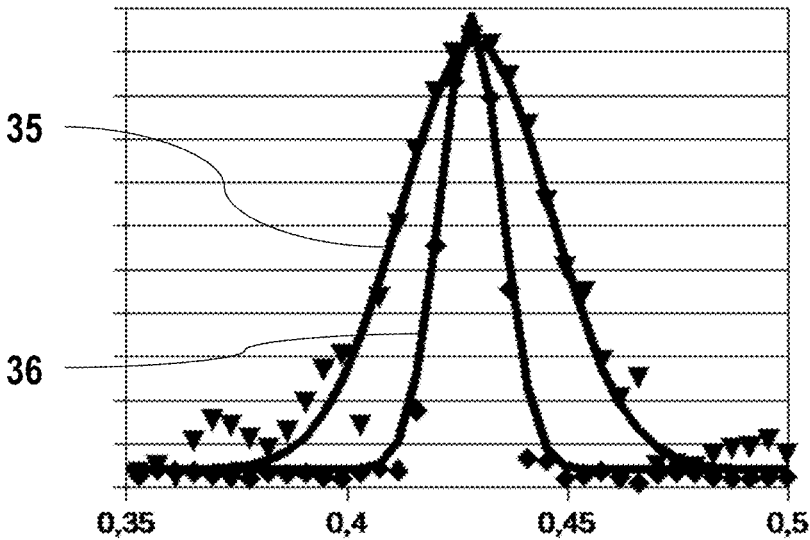
FIG. 10: shows an evaluation originating from a detail from FIG. 9.

One of the peaks from FIG. 9 is shown with higher resolution in the z direction in FIG. 10. The wider peak 35, the mathematical approximation of which is identified by the triangles, corresponds to the measured values from FIG. 9. The expansion of the peak follows from the group-velocity dispersion which underlies the broadband OCT light within the material of the entry body 30. If the group-velocity dispersion is calculated out, a narrower peak 36 thus results, which corresponds to the axial resolution in an air path measurement.

Figure 11:
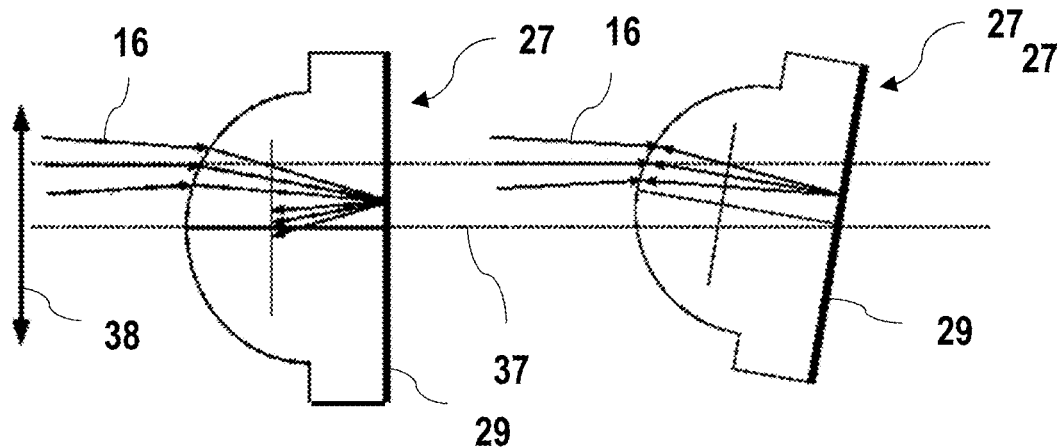
FIG. 11: two different positions of the first test object in the OCT beam path.

FIG. 11 shows two different positions that the first test object 27 can have relative to the optical axis 37 of the OCT beam path 16. The test object 27 shown in the figure on the left is aligned with the optical axis 37 so that the optical axis 37 extends centrally through the first test object 27 and meets the layer structure 29 at a right angle.

The test object 27 shown in the FIG. 11 on the right is tilted relative to the optical axis 37, so that the center axis of the first test object 27 forms an angle with the optical axis 37 that is significantly different from 0°. For both positions, a section of an OCT beam path 16 is indicated, which is shifted in the scanning direction 38 relative to the optical axis 37. The illustration makes it clear that the tilting of the first test object does not have a negative effect on the measurement result. This insensitivity to adjustment is an advantage over alternative methods in which the OCT beam path 16 is reflected at a simple mirror surface.

Figure 12:
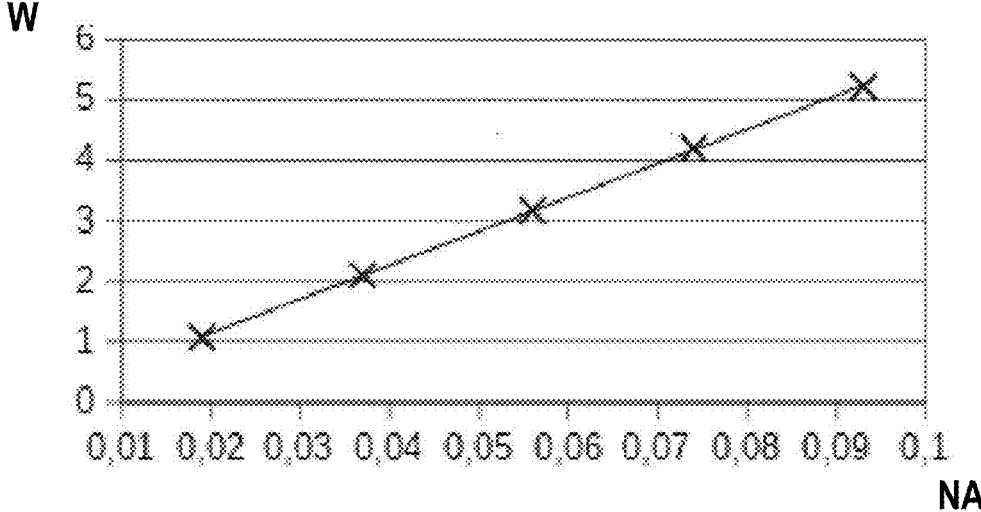
FIG. 12: an illustration of the linear relationship between the scan width of the measurement and the numeric aperture of the OCT device.

While using the method according to the invention, it has been found that there is a linear relationship between the scan width W and the numerical aperture NA of the OCT device 14. The linear relationship between the scan width W and the numerical aperture NA of the OCT device 14 is illustrated in FIG. 12. The scan width W indicates how far the OCT beam path 16 can be shifted in the scanning direction 38 without the OCT signal disappearing. The scan width W is a value that can be easily determined. It is an advantage of the method according to the invention that this linear relationship makes it easy to determine the numerical aperture NA of the OCT device 14.

The invention claimed is:

1. A method for testing an OCT device (14), in which a first test object (27) is arranged in an OCT beam path (16) of the OCT device (14), wherein the first test object (27) comprises a layered structure (29) made of a plurality of planar transparent layers and an entry body (30), wherein OCT light emitted by the OCT device (14) enters the entry body (30) via an entry surface and propagates through the entry body (30) up to the layered structure (29), and wherein the entry surface of the entry body (30) is shaped as a lens surface (31), wherein the OCT light is convergent before entering the lens surface (31) and is focused by the first test object (27) within the layered structure, said method determining one or more of the following parameters of the tested OCT device: axial depth of the measurement window, OCT roll-off, numerical aperture, OCT sensitivity, signal-to-noise ratio, and image curvature.

2. The method of claim 1, wherein the plurality of transparent layers of the layered structure (29) have a thickness between 20 μm and 500 μm, preferably between 50 μm and 200 μm.

3. The method of claim 1, wherein the plurality of transparent layers of the layered structure (29) alternately consist of a first material and a second material.

4. The method of claim 1, wherein each of the plurality of transparent layers is constructed of a material having an index of refraction and an index of refraction difference between the materials of two adjoining layers of the layered structure (29) is less than 0.1, preferably is less than 0.075, more preferably is less than 0.05.

5. The method of claim 1, wherein an index of refraction difference between a material of the entry body (30) and a layer of the layered structure (29) adjoining the entry body is less than 0.1, preferably is less than 0.075, more preferably is less than 0.05.

6. The method of claim 1, wherein the entry surface of the entry body (30) lies outside a measuring window of the OCT device (14).

7. The method of claim 1, wherein the lens surface (31) is shaped so that a distance between a focal position (24) of the OCT beam path (16) and a reference plane (23) of the OCT measurement is reduced by at least 30%, more preferably is reduced by at least 50%, more preferably is reduced by at least 70% in comparison to a test object which has a planar entry surface instead of the lens surface (31).

8. The method of claim 1, wherein a size of an image field of an OCT measurement of the OCT device (14) is determined on the basis of a test structure of a second test object (26).

9. The method of claim 8, wherein the first test object (27) and the second test object (26) are matched to one another so that the OCT beam path (16) is focused on a test surface of the second test object (26) when a contact surface (33) of the second test object (26) is arranged at a predetermined axial distance to the OCT device (14), and that the OCT beam path (16) is focused within the layered structure (29) of the first test object (27) when the first test object (27) is arranged in the OCT beam path (16) instead of the second test object (26) and a contact surface (34) of the first test object has the same predetermined axial distance to the OCT device (14).

10. The method of claim 1, wherein a numerical aperture (NA) of the OCT device (14) is determined on the basis of a functional relationship between a scan width (W) of an OCT measurement of the OCT device (14) and the numerical aperture (NA) of the OCT device (14).

11. The method of claim 1, wherein information about an OCT sensitivity of the OCT device (14) is obtained by means of a measurement with the first test object (14).

12. A test object for use in testing an OCT device (14), comprising a layered structure (29) made up of a plurality of layers and an entry body (30), wherein the layered structure (29) and the entry body (31) consist of materials transparent to OCT light, an entry surface of the entry body is shaped as a lens surface (31) configured to focus a convergent beam within the layered structure (29), wherein an interface formed between each of two adjacent layers of the layered structure is a planar surface.

\* \* \* \* \*